United States Patent [19]
Gillett et al.

[11] Patent Number: 5,402,517
[45] Date of Patent: Mar. 28, 1995

[54] APPARATUS FOR EMITTING A VOLATILE CHEMICAL AGENT BY HEATING AND MEANS FOR ADJUSTING A SPACING BETWEEN A HEATER AND THE CHEMICAL AGENT TO REGULATE THE RATE OF VAPORIZATION

[75] Inventors: Colin Gillett, Wigan; Michael J. Hampshire, Salford; Geoffrey R. Hammond, Hull, all of United Kingdom

[73] Assignee: Reckitt & Colman Products Limited, London, England

[21] Appl. No.: 877,952

[22] Filed: Apr. 29, 1992

[30] Foreign Application Priority Data

May 1, 1991 [GB] United Kingdom ............... 9109442

[51] Int. Cl.⁶ .................................................. A61L 9/02
[52] U.S. Cl. ......................... 392/386; 392/390; 392/392
[58] Field of Search .............. 392/386, 390–395, 392/403–407; 422/125; 219/432, 433; 239/34, 44, 135, 136, 53, 55, 56, 57

[56] References Cited

U.S. PATENT DOCUMENTS

| | | | |
|---|---|---|---|
| 2,588,471 | 3/1952 | Bauer | 422/125 |
| 3,431,393 | 3/1969 | Katsuda | 392/391 X |
| 3,948,445 | 4/1976 | Andeweg | 422/125 |
| 4,769,528 | 9/1988 | Von Philipp et al. | 392/390 |
| 5,115,975 | 5/1992 | Shilling | 239/53 |

FOREIGN PATENT DOCUMENTS

| | | |
|---|---|---|
| 025264 | 2/1988 | European Pat. Off. |
| 296807 | 12/1988 | European Pat. Off. |
| 334785 | 9/1989 | European Pat. Off. |
| 404770 | 1/1934 | United Kingdom ............... 392/390 |
| 1123922 | 9/1965 | United Kingdom |
| 1429032 | 3/1976 | United Kingdom |
| 2057884 | 4/1981 | United Kingdom |
| 2097257 | 11/1982 | United Kingdom |
| 2117639 | 10/1983 | United Kingdom |
| 2139895 | 11/1984 | United Kingdom |
| 2195250 | 4/1988 | United Kingdom |

*Primary Examiner*—Teresa J. Walberg
*Attorney, Agent, or Firm*—Salter & Michaelson

[57] ABSTRACT

An apparatus for emitting a chemical agent includes a housing defined by first and second co-axial housing sections received in end-to-end engagement, a heating element in the second housing section. The heat supplied to the chemical agent is varied so that the rate of vaporization can be controlled. The first housing section includes a vented base portion and a wall portion connected to the base portion so as to define a recess for receiving a volatile chemical agent. The chemical agent or a carrier therefor is secured within the recess. The second housing section includes a solid base portion and a wall portion connected to the base portion. An electric heater element is imbedded within the base portion of the second housing section so that it is electrically isolated from the base surface. The wall portions of each section are received in co-axial engagement so that the chemical agent is adjacent to the heated base. The spacing is varied by relatively movable cooperating formations on the wall portions of the two housing sections which guide and facilitate movement of the first housing section with respect to the second housing section. In a preferred embodiment the cooperating formations are cooperating threads on the surfaces of the wall portions.

9 Claims, 1 Drawing Sheet

APPARATUS FOR EMITTING A VOLATILE CHEMICAL AGENT BY HEATING AND MEANS FOR ADJUSTING A SPACING BETWEEN A HEATER AND THE CHEMICAL AGENT TO REGULATE THE RATE OF VAPORIZATION

This invention relates to an apparatus for emitting a chemical agent and particularly but not exclusively to an apparatus for emitting a fragrance or an insecticide.

It is known to provide a fragrance in gel form in a plastics moulding sealed by a temperature sensitive semi-permeable membrane. A 1.32 watt heater consisting of a thin metallic helical filament wound on a fibrous core is provided in the moulding. The heater produces a temperature of approximately 55° C. at the base of the gel container. When heated the semi-permeable membrane acts to emit the fragrance. However, the amount of fragrance emitted per unit time may not be varied by this known device.

The present invention has been made from a consideration of this problem.

According to the present invention, there is provided apparatus for emitting a chemical agent consisting of a housing defined by first and second co-axial housing sections received in end-to-end engagement, a heating element in the second housing section, and means for controlling the heat supplied to the chemical agent so that the rate of vaporization of the chemical agent can be controlled. The first housing section includes a vented base portion and a wall portion connected to the base portion so as to define a recess for receiving a volatile chemical agent. Means are provided for securing the chemical agent or a carrier therefor within the recess. The second housing section includes a solid base portion and a wall portion connected to the base portion. An electric heater element is imbedded within the base portion of the second housing section so that it is electrically isolated from the base surface. The wall portions of each section are received in coaxial engagement so that the chemical agent enclosed within the housing and is positioned adjacent to the heated base. The means for varying the spacing consists of relatively movable cooperating formations on the wall portions of the two housing sections which guide and facilitate movement of the first housing section with respect to the second housing section thereby regulating the spacing between the chemical agent and the heating element. In a preferred embodiment, the cooperating formations consist of cooperating threads on the surfaces of the wall portions.

In a preferred embodiment of the invention the means for varying the heat supplied to the container comprises means for moving the container relative to the heater means such as relatively movable cooperating formations.

The apparatus may comprise at least two parts, one of the parts being movable relative to the other part. One part may comprise and/or be secured to the heater means and the other part may comprise and/or be secured to the container. The two parts may comprise cooperating screw threads. The heater means is preferably electrically powered. The heater means may comprise at least one resistor which may be in series with a light output device. The light output device may also act as a fuse. Means may be provided, for example on the part of the apparatus comprising the heater means, for indicating the distance between the heater means and the container. This may consist of a marking such as a scale or more preferably a triangular shaped marking.

The apparatus may comprise an absorbent material in order to absorb any chemical agent which may leak from the container.

The container may comprise any suitable chemical agent, preferably in a fluid form, such as at least one of a fragrance or an insecticide.

In order that the invention may be more readily understood a specific embodiment thereof will now be described by way of example only with reference to the accompanying drawings in which.

Figure 1:
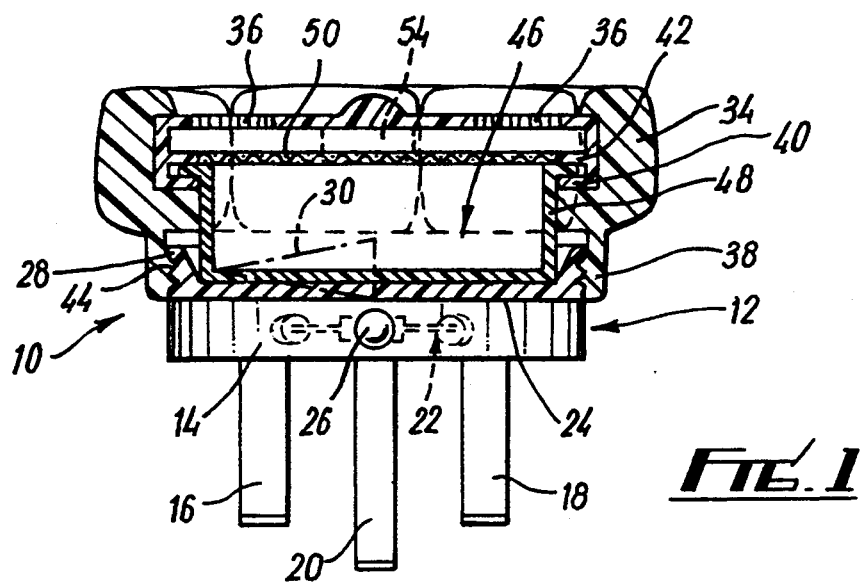
FIG. 1 is a cross sectional view of one apparatus in accordance with the invention.
Figure 2:
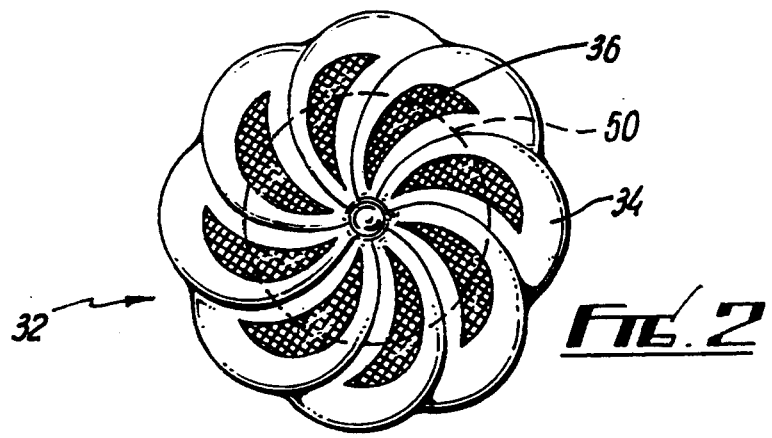
FIG. 2 is a plan view of the apparatus of FIG. 1.
Figure 3:
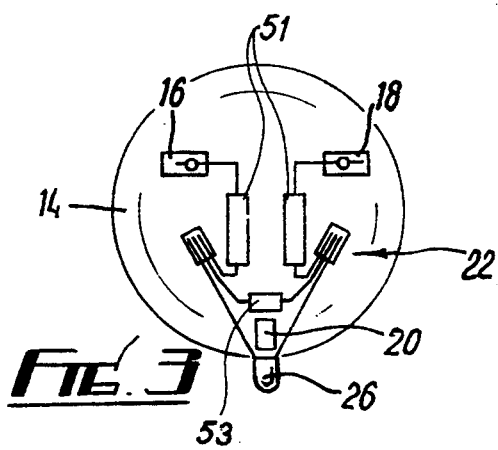
FIG. 3 is a plan view of the heater means of the apparatus of FIGS. 1 and 2.
Figure 4:
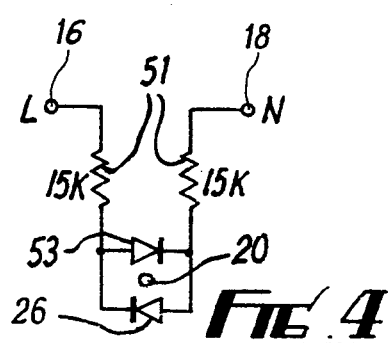
FIG. 4 is a circuit diagram of the heater means of FIG. 3.

Referring to the drawings an apparatus 10 for emitting a chemical agent comprises a housing made substantially of 50% glass-filled, high impact nylon 6 plastics. The housing has a lower part 12 having a cylindrical body 14. Live, neutral and earth electrical pins 16,18,20 extend from the body 14 in a manner conventional for a United Kingdom 240 V a/c mains powered domestic electrical appliance. The live pin 16 and neutral pin 18 are connected to the circuitry of a heating means 22 which is embedded about 2 mm below the surface 24 of the cylindrical body 14. The circuitry of the heater means 22 is shown in FIG. 4. The circuit comprises two 15K ohm resistors 51 in series with a light emitting diode (LED) 26. Preferably the tails from the resistors are not cut short and large oversized crimps are used thus spreading more metal in the hot zone increasing dissipation and providing more uniform heating. A diode 53 is provided across the LED in the opposing polarity to the LED. The provision of two 15K ohm resistors rather than one 30 ohm resistor is considered advantageous in that this doubles the power dissipation and likewise increases heat generated by doubling the element area. Further the second resistor provides a convenient connection to one of the pins of the LED without substantially increasing the cost. Failure of a single component to a short circuit will also not provide excessive current.

The presence of an operating indicator light via the LED is considered advantageous. The current required by the heater for 240 v a/c operation is about 8 mA. As this falls within the normal operating range of LEDs the LED can conveniently be incorporated into the circuit. Furthermore the LED is designed with a fine filamentary contact to the semiconductor surface and on excessive current overload the LED should fail to an open circuit condition thereby acting as a fuse. It is considered that a separate fuse will not be necessary.

The LED produces light only on the forward conduction cycle, and typically will drop about 2.5 volts. Hence at 8 mA the power dissipation for the forward half cycle is 10 mWatts. On the reverse cycle the same current of 8 mA will flow and a voltage of about 6 volts is likely, giving a power dissipation of 24 mWatts. The total dissipation is, therefore, 34 mWatts, and is within the capabilities of most of the larger 3 mm diameter LEDs, which are typically rated at 40 mWatts. A further diode is preferably used to take the reverse current with a volts drop of say 1 volt giving a reverse dissipation of only 4 mWatts. The further diode allows a more efficient LED to be used to increase the light output. However, the extra diode component must be fitted the correct way round in relation to the orientation of the LED, the direction of which is irrelevant as regards the live neutral.

An upstanding wall 28 is provided around the periphery of the cylindrical body 14. A screw thread is provided on the exterior surface of the upstanding wall 28.

The upper part 32 of the apparatus comprises an aesthetically pleasing hollow cover 34, the cover 34 having a depending wall 38. Perforations 36 are provided in the cover for the release of the fragrance. Two spaced apart members 40,42 extend inwardly from the cover 34. A screw thread 44 is provided on the interior of the depending wall 38 for cooperation with the screw thread of the upstanding wall 28 such that the upper and lower parts 32 and 12 respectively, may be moved relative to each other in a controlled manner by way of a twisting movement.

A right angled triangular marking 30 is provided on one part of the exterior surface of the cover 34. The two perpendicular sides of the triangle 30 extend vertically and horizontally in the orientation of the apparatus as illustrated. When fully engaged the vertical line of the triangular mark 30 is in line with the LED. On rotation of the cover a smaller area of the triangle is aligned with the LED.

A polypropylene container 46 comprises a cylindrical housing 48 having a flange extending outwardly from the top of the cylindrical housing 48. A temperature sensitive semi-permeable membrane 50 is provided across the top of the cylindrical housing 48. In use the membrane 50 is protected from physical damage by the cover 34. About 6 ml of a liquid fragrance are provided in the cylindrical housing 48. In normal use this amount of fragrance is estimated to last for about 30 days after which time the container is replaced. Fine capillary grooves (not shown) are provided on the internal sides of the container 46 so that the liquid fragrance will rise to wet the membrane, so enabling the emission of fragrance even when the liquid is not in contact with the membrane's surface.

In use, the apparatus is plugged into an electricity supply socket, such as a wall mounted socket, by way of the electrical pins 16,18,20. This activates the heating circuit and the LED will light. The heat supplied by the dissipation of heat from the resistors in the circuit will heat the base of the container 46 and then the fragrance and semi-permeable membrane. As the semi-permeable membrane is temperature sensitive the heating of the membrane will allow release of the liquid fragrance.

The rate of release of the liquid fragrance may be controlled by moving the base of the container 46 relative to the heater.

When fully engaged the base of container 46 is in intimate contact with the heated surface 24 of the cylindrical body 14. As the container 46 is unscrewed a gap appears between the heater and the base and this progressively increases in a controlled manner, thereby increasing the heat losses and reducing the temperature of the fragrance housed in the capsule. Furthermore the separation between the heater and the cylinder and thus the degree of heating and fragrance emission is indicated by the amount of the triangular mark lined up with the LED.

In the apparatus shown the cylinder is heated by the dissipation of about 2 watts to a temperature in the region of 40° C. At this temperature the release of the fragrance through the membrane is appreciable.

With the apparatus illustrated the rate of the release of fragrance is considered to approximately double for every 10° C. rise in temperature.

It is to be understood that the above described embodiment is by way of illustration only. Many modifications and variations are possible.

Additional ventilation may be provided to the heated surface, for example by providing apertures on opposite sides of the cover in order to increase air flow. If the apparatus is to be mounted vertically the apertures are preferably provided at the top and base of the apparatus.

Preferably an absorbent pad 54 is provided in the interior of the apparatus such as on the part of the walls on which no screw thread is provided. The absorbent material would be used to absorb any fragrance which may leak from the container should the membrane be punctured. The pad could be made from foam or felt with sufficient absorptive capacity to hold the maximum amount of fluid provided in the container such as 6 ml in the embodiment described above.

The container may comprise any chemical agent in addition to or in place of the fragrance such as an insecticide.

The electrical connection may be adapted to meet the requirements of any electricity supply.

The filled container may comprise any suitable amount of fluid such as from 1 to 20 mls.

The heater means may be embedded any suitable distance from the surface of the lower part of the apparatus such as a distance in the range from 0.5 to 4 mm.

The apparatus may comprise any suitable material such as any sufficiently heat resistant plastics material.

The containers for the chemical agent may be disposable or re-usable.

We claim:

1. An apparatus for emitting a volatile chemical agent comprising:

a housing defined by first and second co-axial housing sections, said first housing section including a vented base portion and a wall portion connected to the base portion so as to define a recess for receiving said chemical agent, said first housing section further including means for securing said chemical agent within said recess, said second housing section including a base portion and a wall portion connected to the base portion;

heating means imbedded in said base portion of said second housing section so as to be electrically isolated from a surface of said base portion, said wall portion of said first housing section being removably received in engagement with said wall portion of said second housing section such that said chemical agent in said recess is enclosed within said housing and is positioned adjacent said heated base portion of said second housing section; and means for varying an amount of heat supplied to said chemical agent so as to vary the rate of release of said chemical agent, said means for varying said heat comprising relatively movable cooperating formations on the wall portions of the first and second housing sections wherein said cooperating formations guide relative movement of said first and second housing sections and facilitate a change in a spacing between said heated base portion of said second housing section and said chemical agent received in said recess in said first housing section.

2. An apparatus for releasing a chemical agent as claimed in claim 1, wherein the co-operating formations comprise screw threads.

3. An apparatus for releasing a chemical agent as claimed in claim 1, wherein the heater means comprises at least one resistor.

4. An apparatus for releasing a chemical agent as claimed in claim 1, wherein the heater means comprises a light output device which acts as a power indicator and a fuse.

5. An apparatus for releasing a chemical agent as claimed in claim 1, wherein the apparatus comprises means for indicating the distance between the heater means and the container.

6. An apparatus for releasing a chemical agent as claimed in claim 1, wherein the apparatus comprises an absorbant material in order to absorb any chemical agent which may leak from the container.

7. An apparatus for releasing a chemical agent as claimed in claim 1, wherein the chemical agent comprises a fragrance.

8. An apparatus for releasing a chemical agent as claimed in claim 1, wherein the chemical agent comprises an insecticide.

9. An apparatus for releasing a chemical agent as claimed in claim 1, wherein said chemical agent is contained within a carrier, said apparatus including means for securing said carrier within said recess.

* * * * *